US Patent [19] 3,948,621
Cocuzza et al. [45] Apr. 6, 1976

[54] PROCESS FOR THE SIMULTANEOUS SEPARATION OF ETHYLENE OXIDE AND CARBON DIOXIDE FROM THE GASEOUS MIXTURES OBTAINED IN THE DIRECT OXIDATION OF ETHYLENE WITH OXYGEN

[75] Inventors: Gioacchino Cocuzza, Catania; Benedetto Calcagno, Milan; Gianni Torreggiani, Busto Arsizlo (Varese), all of Italy

[73] Assignee: Societa' Italiana Resine S.p.A., Milan; Italy

[22] Filed: Dec. 26, 1973

[21] Appl. No.: 428,570

[30] Foreign Application Priority Data
Dec. 22, 1972 Italy................................ 33442/72

[52] U.S. Cl. ............................ 55/29; 55/30; 55/48
[51] Int. Cl.² .................... B01D 53/14; B01D 19/00
[58] Field of Search ............... 55/29, 30, 48, 51, 64, 55/68

[56] References Cited
UNITED STATES PATENTS
3,531,915  10/1970  Nagel et al........................... 55/64 X
3,676,981   7/1972  Afdahl et al............................ 55/30
3,766,714  10/1973  Cunningham et al................... 55/48

Primary Examiner—Frank A. Spear, Jr.
Assistant Examiner—Ferris H. Lander
Attorney, Agent, or Firm—Sughrue, Rothwell, Mion, Zinn & Macpeak

[57] ABSTRACT

Process for the simultaneous separation of ethylene oxide and carbon dioxide from the gaseous mixtures obtained in the direct oxidation of ethylene with oxygen, comprising
a. cooling the gaseous mixture containing ethylene oxide, unreacted ethylene, water vapour, carbon dioxide and inert gases after addition of methanol to a temperature such that the water vapour present separates in the form of an aqueous methanol solution;
b. washing the obtained gaseous mixture in an absorption zone with methanol, the methanol being fed into the intermediate part of the absorption zone as a main methanol stream and into the upper part as a secondary methanol stream, maintaining the temperature of the secondary methanol stream at least about 30°C lower than that of the main methanol stream and removing from the upper part a gaseous mixture being practically free of ethylene oxide and containing carbon dioxide and ethylene and from the lower part of the absorption zone a solution of ethylene oxide in methanol; and
c. recovering the ethylene oxide from the methanol solution.

12 Claims, 1 Drawing Figure

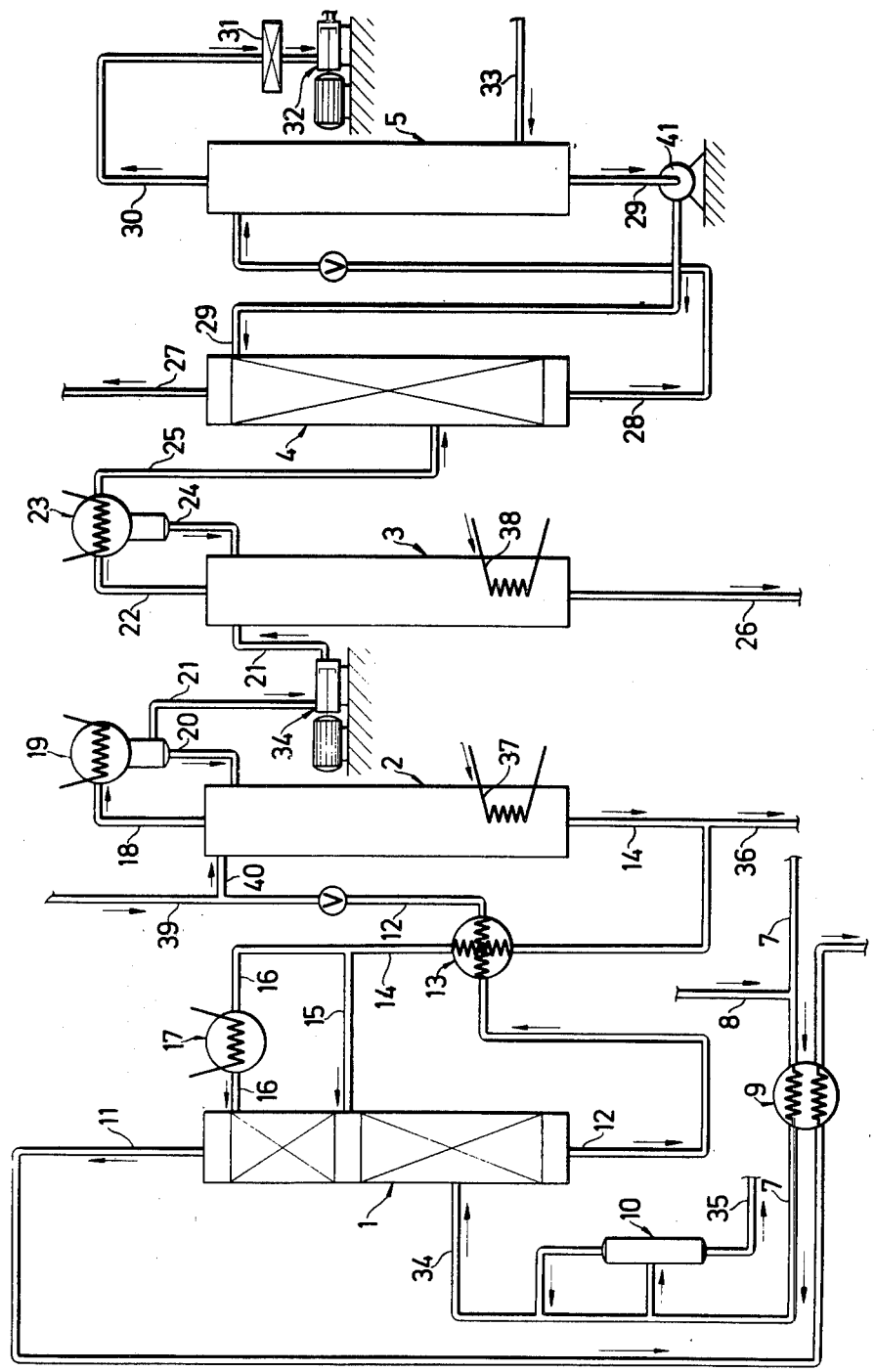

PROCESS FOR THE SIMULTANEOUS SEPARATION OF ETHYLENE OXIDE AND CARBON DIOXIDE FROM THE GASEOUS MIXTURES OBTAINED IN THE DIRECT OXIDATION OF ETHYLENE WITH OXYGEN

BACKGROUND OF THE INVENTION

1. Field of the Invention

The present invention relates to an improved process for the simultaneous separation of ethylene oxide and carbon dioxide from the gaseous mixtures obtained in the direct oxidation of ethylene with oxygen.

In the direct oxidation of ethylene to ethylene oxide two process methods are known one of which comprises the use of air and the other the use of oxygen as oxidizing agent. The oxidation is carried out over a silver catalyst using short residence times and at temperatures of from 150° to 400° C and pressures of from atmospheric pressure to about 30 atmospheres. In view of the danger of explosion a gaseous mixture is employed which contains relatively small quantities of ethylene. The conversion must not be too high in order to safeguard high selectivity. The gaseous mixture leavig the reactor generally contains 1 to 3% by volume of ethylene oxide. The mixture is cooled in a heat exchanger, then compressed and washed with water in a washer (absorber), in order to separate the ethylene oxide. The remaining ethylene is recycled to the process. As by-products of the direct oxidation carbon dioxide and water are obtained; see Kirk-Othmer, *Encyclopedia of Chemical Technology*, 2nd edition, vol. 8 (1965), pages 534 to 542. Therefore one is faced with the problem of eliminating these by-products, in particular the carbon dioxide, or of keeping them to a desired concentration and avoiding their accumulation.

When air is used as oxidizing agent a part of the gaseous mixture leaving the reactor and being free of ethylene oxide is continuously blown off overhead in order to avoid gradual accumulation of inert gases, such as nitrogen. In this way, a fraction of the carbon dioxide corresponding to that continuously produced is eliminated from the reaction gases, with the result that accumulation of this by-product is avoided.

The use of oxygen as oxidizing agent has the advantage of eliminating or at least substantially reducing the blowing off of the washed out reaction gases still containing a small quantity of ethylene. However, in this case a treatment of the reaction gases is necessary in order to eliminate the carbon dioxide. After having been quenched the gaseous mixture leaving the reactor is first washed out with water in order to separate the ethylene oxide in the form of an aqueous solution. The gases which have not been absorbed are subsequently subjected to a treatment with a solution of an alkali metal carbonate or alkanolamine in order to separate the carbon dioxide. The residual gases which contain unreacted ethylene are then recycled to the reactor after previous addition of fresh ethylene and oxygen.

The process for the preparation of ethylene oxide using oxygen as oxidizing agent therefore has essentially the disadvantage of the double treatment of the reaction gases. Moreover, this process requires large quantities of water for the washing out of the reaction gases in the ethylene oxide washer. This leads to the necessity to recycle the lean aqueous solvent leaving the ethylene oxide stripper to the ethylene oxide washer. It is also known that this lean aqueous solvent still contains ethylene oxide in quantities of about 0.05% by weight, owing to the conditions under which the stripping phase is carried out industrially.

Thus, because of the low concentration of ethylene oxide in the reaction gases produced in the direct oxidation of ethylene and because of the presence of residual quantities of ethylene oxide in the lean aqueous solvent, this compound cannot be obtained with satisfactory recovery from the economic point of view under the temperature and pressure conditions under which the washing out of the reaction gases is carried out in practice. Thus, the large quantities of water required and the high heat capacity and heat of vaporization of the water lead to high heat consumptions in the stripping operation.

SUMMARY

It is therefore an object of the present invention to eliminate the above-mentioned disadvantages implied in the preparation of ethylene oxide by direct oxidation of ethylene with oxygen as oxidizing agent and to provide an effective process for the simultaneous separation of ethylene oxide and carbon dioxide from the reaction gases.

The process of the present invention consists essentially in subjecting the gaseous mixtures obtained in the direct oxidation of ethylene with oxygen to a treatment with methanol under conditions such that the simultaneous separation of the ethylene oxide and of the carbon dioxide is achieved.

Thus the present invention provides a process for the simultaneous separation of ethylene oxide and carbon dioxide from the gaseous mixtures obtained in the direct oxidation of ethylene with oxygen, comprising;

a. cooling the gaseous mixture containing ethylene oxide, unreacted ethylene, water vapour, carbon dioxide and inert gases after addition of methanol to a temperature such that the water vapour present separates in the form of an aqueous methanol solution;

b. washing the obtained gaseous mixture in an absorption zone with methanol, the methanol being fed into the intermediate part of the absorption zone as a main methanol stream and into the upper part as a secondary methanol stream, maintaining the temperature of the secondary methanol stream at least about 30° lower than that of the main methanol stream and removing from the upper part a gaseous mixture being practically free of ethylene oxide and containing carbon dioxide and ethylene and from the lower part of the absorption zone a solution of ethylene oxide in methanol; and c. recovering the ethylene oxide from the methanol solution.

For recovering the ethylene oxide the absorbed compounds, i.e. ethylene oxide and carbon dioxide as well as small quantities of ethylene and inert gases, are separated from the methanol solution by desorption and the ethylene oxide is recovered from this gaseous mixture. By operating in this way and by observing the below-stated other conditions one achieves first of all a practically complete separation of the ethylene oxide and simultaneous separation of the carbon dioxide from the gaseous mixture originating from the direct oxidation of the ethylene. This constitutes an advantage over the processes which necessitate two separate stages for the treatment of the gaseous mixture, the first having the purpose of separating the ethylene oxide and the second the purpose of separating the carbon dioxide. Unlike the known processes the process of the present invention also allows practically complete separation of the ethylene oxide in the absorption zone. Finally, a further advantage of the process of the present invention consists in the easy separation of the ethylene oxide from the other gases obtained after desorption from the methanol solution.

DESCRIPTION OF THE PREFERRED EMBODIMENTS

In the attached Figure, the reference 7 indicates the pipe through which a gaseous mixture obtained in the direct oxidation of ethylene is fed from a reactor (not shown) into a heat exchanger 9. This gaseous mixture contains ethylene oxide generally in quantities of from 1 to 3% by volume. The remainder consists of inert gases (mainly nitrogen), unreacted ethylene, oxygen as well as carbon dioxide and water vapour. After leaving the reactor the gaseous mixture is first cooled to temperatures of about 30° C. Subsequently methanol is added through the pipe 8 in a quantity of from two to six times the weight of the water vapour fed with the gaseous mixture through the pipe 7. The added methanol serves to prevent solidification of the water during the subsequent cooling. The gaseous mixture enriched in methanol is then cooled in the heat exchanger 9 to temperatures of about −20° C to cause practically total separation of the water in the form of an aqueous methanol solution in the separator 10. This solution is eliminated from the separator 10 through the pipe 35 and is then passed to a rectification column (not shown in the figure) for recovery of the methanol.

The gaseous mixture containing ethylene oxide, unreacted ethylene, water vapour, carbon dioxide and inert gases is then fed through the pipe 34 to the base of the absorption column 1. Into this column 1 which is operated at pressures of from 10 to 30 kg/cm², a main methanol stream is fed through the pipe 15 and a secondary methanol stream through the pipe 16. The secondary methanol stream is fed to the upper part of the absorption column 1, while the main methanol stream is fed to the intermediate part of the absorption column 1 at a point between the feeding point of the gaseous mixture and that of the secondary stream. A fundamental aspect of the process of the present invention is the maintenance of the secondary methanol stream at a temperature at least about 30° c lower than that of the main stream. Preferably, the temperature of the secondary stream is maintained at values of from about −20° to −60° C and that of the main stream at values of from about +10° to −30° C.

During feeding to the absorption column 1 the weight ratio of the total methanol to the ethylene oxide contained in the gaseous mixture fed through the pipe 34 is about 5:1 to 50:1. Under these conditions and with a weight ratio of the main methanol stream to the secondary methanol stream of from about 1:1 to 6:1 a gaseous mixture which in addition to carbon dioxide, ethylene and inert gases contains less than 0.01% by volume of ethylene oxide, is eliminated through the pipe 11.

The low temperatures maintained in the absorption column 1 by the main methanol stream and in particular the secondary methanol stream increases the absorption capacity of the methanol. In particular, a lower temperature is required at the top of the absorption column in view of the low partial pressures of the compounds to be eliminated. Furthermore, the low temperatures prevailing at the top of the absorption column 1 cause a considerable reduction of the methanol content in the ethylene oxide-free gaseous mixture leaving through the pipe 11. This gaseous mixture is recycled to the reactor after previous addition of fresh oxygen and ethylene. A methanol solution containing ethylene oxide, carbon dioxide and smaller quantities of ethylene and inert gases is discharged from the absorption column 1 through the pipe 12. This methanol solution, after heat exchange in a heat exchanger 13, is fed to the top of a desorption column 2 where the desorption of the ethylene oxide and of the other normally gaseous compounds occurs. For this purpose the methanol solution is heated by means of coils 37. The desorption column 2 is preferably operated at temperatures of from about 65° to 85° C and at pressures of from about 1 to 2 kg/cm². A solution of a potassium alkoxide preferably a solution of potassium methoxide in methanol, is fed through the pipe 39 to the pipe 12 in order to neutralize any acidity present in the methanol solution. The methanol solution obtained is subsequently fed through the pipe 40 to the desorption column 2.

The methanol free of the gaseous compounds is removed at the base of the desorption column 2 through the pipe 14 and is first subjected to heat exchange in the heat exchanger 13 and is subsequently partly fed through the pipe 15 to the absorption column 1 as main methanol stream. The residual methanol after previous cooling in the heat exchanger 17 is fed through the pipe 16 to the absorption column 1 as secondary methanol stream.

A purge also occurs through the pipe 36 in order to avoid the accumulation of major quantities of products of the reaction of the methanol with ethylene oxide which are formed, though in small quantities, under the reaction conditions used.

At the top of the desorption column 2 a gaseous mixture which in addition to ethylene oxide and carbon dioxide still contains small amounts of methanol is removed through the pipe 18. This gaseous mixture is cooled in the heat exchanger 19 to a temperature of about 0° C in order to achieve a practically complete condensation of the methanol. This methanol is recycled through the pipe 20 to the desorption column 2. The gaseous mixture is compressed in a compressor 34 and is fed through the pipe 21 to the upper part of a rectification column 3. The rectification column 3 which may also be defined as recovery column, is operated at temperatures of from about 30° to 60° C, measured at the base of the column, and at pressures of from about 2 to 5 kg/cm². In this rectification column 3 a desorption of the ethylene oxide occurs. For this purpose the ethylene oxide is heated in the rectification column 3 by means of coils 38. At the base of the rectification column 3 liquid ethylene oxide is removed through the pipe 26 and then purified in a manner known per se, e.g. by rectification under pressure, residual methanol which is still present in the gaseous mixture fed through the pipe 21 as well as products of the reaction of methanol with ethylene oxide being separated at the base.

The gases removed at the top of the rectification column 3 through the pipe 22 are cooled in the heat exchanger 23 to a temperature of about −50° C in order to condense the ethylene oxide carried along. This liquid ethylene oxide is recycled through the pipe 24 to the top of the rectification column 3 and is used as washing liquid for the fed gaseous mixture. The residual gases discharged through the pipe 25 are subjected to treatments for the recovery of the ethylene. For this purpose the gaseous mixture is fed to the base of the extraction column 4, while a solvent for ethylene is fed through the pipe 29 to the top of the extraction column 4. Solvents suitable for this purpose are high-boiling hydrocarbon mixtures, such as diesel oils having initial boiling points of from about 140° to 180° C and a density of from 0.82 to 0.85 g/ml. The extraction column 4 is operated at temperatures of from about 0° to 20° c and at pressures of from about 3 to 5 kg/cm². A gaseous mixture consisting of carbon dioxide and nitrogen is removed through the pipe 27.

The ethylene-containing diesel oil is discharged through the pipe 23 and fed to the top of the stripper 5. Nitrogen is fed to the stripper 5 through the pipe 33. The stripper 5 is operated at temperatures of from about 0° to 20° C and at pressure of from about 1 to 2 kg/cm². The ethylene is removed at the top of the stripper through the pipe 30, fed to a filter 31 in order to eliminate the traces of diesel oil, the filter being e.g. filled with activated carbon, subsequently compressed through the compressor 32 and recycled to the reactor.

In order to achieve the low temperatures necessary in the heat exchangers 17, 19 and 23 the inventive process provides a normal refrigeration cycle operated with ammonia or low boiling perfluoro-alkanes.

According to a characteristic of the process of the present invention the water is separated from the ethylene oxide-containing reaction gases before the methanol is washed out in the absorption zone. In this way, the gases recycled to the reactor for direct oxidation are practically free of water vapour. This is advantageous since water vapour affects the direct oxidation of ethylene to ethylene oxide.

The invention is further illustrated by the following non-limiting example.

EXAMPLE

With reference to the attached Figure, a gaseous mixture originating from the reactor for the oxidation of ethylene with oxygen (purity of the oxygen 99.5%) is fed through the pipe 7 to the heat exchanger 9. This gaseous mixture which has previously been quenched in a heat exchanger cooled with brine has the following composition, expressed in percent by volume:

ethylene oxide 1.5%, carbon dioxide 10%, water 0.2%, ethylene 5%, oxygen 4%, methane and ethane 1%, the remainder consisting of nitrogen with smaller quantities of argon. (Due to the circulation the gaseous mixture continuously accumulates nitrogen; therefore the process requires a limited blowing off in order to separate excess nitrogen).

Methanol is fed through the pipe 8 in such quantities that the weight ratio of methanol to the water vapour contained in the gaseous mixture is 5:1. The obtained gaseous mixture is cooled in the heat exchanger 9 to a temperature of −15° C, the gaseous mixture being free of ethylene oxide and originating from the pipe 11 being used for cooling. Downstream from the heat exchanger 9 is a centrifugal separator of the cyclone type in which an aqueous methanol solution is separated. This methanol solution is discharged through the pipe 35 and passes on for recovery of the methanol by rectification.

The dehydrated gaseous mixture (content of water vapour equal to 2.5% with respect to the initial value) is fed to the lower part of the column 1 (20 m high). This absorption column 1 is a packed column which is operated at a pressure of 20 kg/cm². Methanol is fed to the absorption column through the pipes 15 and 16. The weight ratio of the total methanol to the ethylene oxide contained in the gaseous mixture is 25:11. The methanol is fed as a secondary stream (pipe 16) at a temperature of −50° C to the top of column 1 and as main stream (pipe 15) at a temperature of −10° C to the column 1 at a height 5 metres lower than the feed of the secondary stream. The weight ratio of the secondary methanol stream to the main methanol stream is 1:3.

A gaseous mixture containing 8.5% by volume of carbon dioxide and 0.005% by volume of ethylene oxide is separated at the top of the absorption column 1 through the pipe 11. This mixture having a temperature of about −40 °C is fed to the heat exchanger 9 where it is heated by means of the gaseous mixture fed through the pipe 7.

At the base of the absorption column 1 a methanol solution enriched in ethylene oxide and carbon dioxide is discharged through the pipe 12. This solution is heated in the heat exchanger 13 and subsequently fed to the desorption column 2. Prior to feeding to the desorption column 2 a solution of 5% of potassium methoxide in methanol is fed through the pipe 39. The weight ratio of the solutions fed through the pipes 12 and 39 is 100:1. In this way, the pH-value of the solution fed through the pipe 40 is maintained at about 7.

The desorption column 2 is operated at a pressure of 1.1 kg/cm² and at a temperature of 70° C at the base. The gaseous mixture recovered at the top of the desorption column 2 is first cooled in the heat exchanger 19 in order to practically fully condense the methanol vapours carried along. The methanol is recycled through the pipe 20 to the desorption column 2. A gaseous mixture of 0° C having the following composition in percent by volume is recovered from the heat exchanger 19 through the pipe 21:

carbon dioxide 42%, ethylene oxide 42%, ethylene 4%, methanol 3.5%, the remaining consisting essentially of nitrogen.

This gaseous mixture is compressed in a compressor 34 and is subsequently fed to a rectification column 3 at the height of the second or third base, which is operated at a pressure of 5 kg/cm² and at a base temperature of 60° C. The gaseous mixture leaving the rectification column 3 through the pipe 22 is cooled to a temperature of −50° C in a heat exchanger 23 the ethylene oxide contained in said gaseous mixture being condensed and recycled through the pipe 24 as liquid to the top of the rectification column at the height of the first base. A gaseous mixture is removed through the pipe 25, which contains carbon dioxide, ethylene and non-condensable gases, mainly nitrogen. The ethylene oxide content in this gaseous mixture is less than 1% by volume.

Ethylene oxide containing small quantities of methanol is removed from the base of the rectification column 3 through the pipe 26 and further purified in the usual manner. The ethylene-containing gaseous mixture is further processed in an extraction column 4. In the extraction column 4 the ethylene is washed out with diesel oil (initial distillation point 170° C) and in a stripper 5 the ethylene is stripped from the ethylene-containing diesel oil with nitrogen. The extraction column is a packed column. It is operated at a temperature of 10° C and at a pressure of 4 kg/cm². More than 90% of the ethylene fed through the pipe 25 are absorbed in the extraction column 4. At the top of the extraction column 4 a gaseous mixture is discharged through the pipe 27, which consists of more than 80% by volume of carbon dioxide and smaller quantities of nitrogen and oxygen and has an ethylene content of less than 1% by volume. The ethylene-containing diesel oil is fed through the pipe 28 to the top of the stripper 5 equipped with plates. The stripper is operated at a pressure of 1 kg/cm². For the desorption of the ethylene nitrogen is fed through the pipe 23 to the lower part of the stripper 5. In this way, a gaseous mixture containing about 10% by volume of ethylene as well as nitrogen is removed through the pipe 30 and freed from the traces of diesel oil in the filter 31.

Subsequently, the gaseous mixture is compressed in a compressor 32 to 25 kg/cm² and recycled to the reactor for direct oxidation. The diesel oil free of ethylene is removed through the pipe 29 and fed to the top of the extraction column 4 through the pump 41.

What we claim is:

1. An improved process for the simultaneous separation of ethylene oxide and carbon dioxide from the gaseous mixtures obtained in the direct oxidation of ethylene with oxygen, comprising
   a. cooling the gaseous mixture containing ethylene oxide, unreacted ethylene, water vapour, carbon dioxide and inert gases after addition of methanol to a temperature such that the water vapour present separates in the form of an aqueous methanol solution;
   b. washing the obtained gaseous mixture in an absorption zone with methanol, the mehthanol being fed into the intermediate part of the absorption zone as a main methanol stream and into the upper part as a secondary methanol stream, maintaining the temperature of the secondary methanol stream at least about 30° C lower than that of the main methanol stream and removing from the upper part a gaseous mixture being practically free of ethylene oxide and containing carbon dioxide and ethylene and from the lower part of the absorption zone a solution of ethylene oxide in methanol; and
   c. recovering the ethylene oxide from the methanol solution.

2. A process as recited in claim 1, wherein methanol is added to the gaseous mixture originating from the direct oxidation of ethylene in a quantity of from 2 to 6 times the weight of the water vapour contained in said mixture.

3. A process as recited in claim 1, wherein the aqueous methanolic solution is separated by cooling to a temperature of about −20° C.

4. A process as recited in claim 1, wherein the washing of the methanol in the absorption zone is carried out at pressures of from about 10 to 30 kg/cm².

5. A process as recited in claim 1, wherein methanol is fed to the absorption zone as the secondary methanol stream at a temperature of from about −20° to −60° C.

6. A process as recited in claim 1, wherein methanol is fed to the absorption zone as the main methanol stream at a temperature of from about +10° to −30° C.

7. A process as recited in claim 1, wherein in the absorption zone a weight ratio between the total methanol and the ethylene oxide contained in the gaseous mixture introduced is adjusted to values of from about 5:1 to 50:1.

8. A process as recited in claim 1, wherein the weight ratio between the main methanol stream and the secondary methanol stream fed into the absorption zone is adjusted to values of from about 1:1 to 6:1.

9. A process as recited in claim 1, wherein the ethylene oxide of step (c) is recovered from the methanol solution by heating the solution at temperatures of from about 65° to 85° C.

10. A process as recited in claim 9, wherein the heating is carried out at pressures of from about 1 to 2 kg/cm².

11. A process as recited in claim 9, wherein a solution of a potassium alkoxide is fed into the methanol solution in order to neutralize any acidity present.

12. A process as recited in claim 11, wherein the potassium alkoxide is potassium methoxide.

* * * * *